United States Patent [19]

Bhate et al.

[11] Patent Number: 4,896,669
[45] Date of Patent: Jan. 30, 1990

[54] DILATATION CATHETER

[75] Inventors: Anandkumar Bhate, North Bergen; David Catlin, Middletown, both of N.J.

[73] Assignee: Meadox Medicals, Inc., Oakland, N.J.

[21] Appl. No.: 239,081

[22] Filed: Aug. 31, 1988

[51] Int. Cl.$^4$ ............................................. A61M 29/02
[52] U.S. Cl. ........................................ 606/194; 604/96
[58] Field of Search ............... 128/344, 348.1; 604/96, 604/103

[56] References Cited

U.S. PATENT DOCUMENTS

| | | | |
|---|---|---|---|
| 3,837,347 | 9/1974 | Tower ............................ | 128/344 X |
| 4,351,341 | 9/1982 | Goldberg et al. ................ | 128/348.1 |
| 4,702,252 | 10/1987 | Brooks et al. ................... | 128/344 |
| 4,706,670 | 11/1987 | Andersen et al. ............... | 128/344 |

Primary Examiner—Dalton L. Truluck
Attorney, Agent, or Firm—Blum Kaplan

[57] ABSTRACT

A dilatation catheter having an outer tubular balloon portion with length-wise circumferential crimps having at either end transition portions with longitudinal crimps across the axis and an inner catheter is provided. The distal transition portion is fastened to the distal end of the inner catheter tube which extends beyond the distal end of the outer tube and the balloon portion while the proximal transition portion is connected to the distal end of the outer catheter tube. The balloon portion expands readily to a predetermined diameter while undergoing little change in length with an extension of the transition portions so that relative movement of the inner and outer catheter tubing is not required. Accordingly, minimum shear forces occur at the interface of the expanded balloon surface and the interior vessel wall.

33 Claims, 3 Drawing Sheets

DILATATION CATHETER

BACKGROUND OF INVENTION

This invention relates to catheters and more particularly to dilatation catheters which have an inflatable balloon portion which will not be displaced axially when inflated in a blood vessel to increase the patency thereof.

It is a well known medical practice to use balloon catheters for enlarging the luminal diameter of a blood vessel, for example, at a point of stenosis such as is produced by an accumulation of plaque. In one procedure, known as percutaneous transluminal coronary angioplasty, the patent is viewed on an x-ray imaging screen while a flexible guide wire is first introduced through the skin into a coronary artery of a patient, and is so manipulated as to travel therein and penetrate the lumen of an occluded portion of the artery. A guide catheter is then fed along the guide wire to a point in the artery which is just proximal of the occlusion. Finally, the dilatation catheter is sent along the guide wire, within the guide catheter, and into the artery of the patient to position the balloon portion of the catheter in the occluded portion of the artery.

One such dilatation catheter has a flexible shaft which includes an inner tube, or cannula, which can pass freely along the guide wire and a flexible outer tube which surrounds the inner tube and has an inner diameter which is somewhat larger than the outer diameter of the inner tube. A flexible balloon portion at the distal end of the outer shaft is sealed to the distal end of the inner tube. The balloon portion is capable of expansion when fluid under pressure is directed into the space between the outer tube of the shaft and the inner tube whereas the outer tube of the shaft is relatively more rigid and is not capable of such expansion.

When the balloon portion of the catheter has been correctly positioned as seen on the x-ray imaging screen, a radiopaque, fluid contrast medium is introduced under pressure into the space between the inner and the outer tubes to expand the balloon portion which presses against the occluded matter on the inside of the artery. The expansion of the balloon must be carefully controlled to prevent possible over-expansion and over-stressing of the wall of the catheter which might cause it to rupture, while putting sufficient force on the blood vessel to accomplish the objectives of the procedure. When the desired enlargement of the occluded portion of the artery is completed, the pressure on the fluid inside the catheter is relieved, the balloon shrinks, and the catheter is then removed.

In one catheter of the above type, the proximal end of the catheter is fitted to a mount which receives the proximal ends of the inner tube and of the shaft tube and seals them in spaced-apart relationship, while providing a passageway for supplying fluid under pressure to the space therebetween. When the catheter is pressurized, the inner tube shifts its position to accommodate the decrease in the length of the balloon which occurs when the balloon expands. Upon release of pressure in the catheter, the inner tube tube is returned to it original distal position so that the movement of the inner tube aids in reducing the diameter of the balloon to approximately its original diameter, easing removal of the catheter from the blood vessel.

Some of the known catheters of this type exhibit axial shrinkage of the balloon portion during inflation. In some prior art catheters, non-uniform axial shrinkage of the balloon during inflation results in undesirable curving of the distal portion of the balloon. Accordingly, there is a need for a balloon catheter in which the external surface of the balloon portion does not rotate or change dimensions longitudinally during inflation and which, at the same time, does not experience significant axial displacement during inflated. Concomitant with the foregoing is a need for dimensional stability of the inflated balloon so that there is very little further expansion and stretch after the balloon reaches the desired inflation dimensions. In this way, overexpansion of the balloon and consequent damage to the vessel wall is minimized if the specified pressure is exceeded by mistake. The balloon which meets the foregoing needs should also be capable of rapid deflation and of subsequent complete recovery of original dimensions so as to allow easy and prompt retrieval when the procedure has been completed.

SUMMARY OF THE INVENTION

Generally speaking, in accordance with the invention, the foregoing requirements are met by a catheter having an expandable balloon portion formed with length-wise circumferential pleat-like crimps which provide a high degree of circumferential compliance up to a predetermined limit of expansion, e.g., the point at which the pleats are completely unfolded. The distal and proximal connecting portions are crimped into longitudinal pleat-like folds across the axis and provide a precalculated degree of compliance in the axial direction of the shaft.

When fluid under pressure is supplied to the catheter via a space between an inner and outer tubing, the balloon portion expands radially, but has little change in longitudinal dimension. Such little shortening as occurs at the two ends of the balloon is accommodated by expansion of the connecting portions with substantially no change in radial dimension. The walls of the expanding balloon portion and of the connecting portions are made of a fabric substrate which has been crimped and is treated with an elastomeric material. The elastomeric material resists penetration by the pressurizing fluid without interfering with the desired expansion of the balloon. The fabric substrate may be coated or impregnated with elastomer or an inner and outer sleeve of the elastomer may be placed about the fabric substrate. The elastomer provides elasticity to the walls of the balloon and the connecting portions to facilitate rapid deflation and subsequent complete recovery of original dimensions. In addition, the elastomer provides a smooth outer surface for the balloon portion and the connecting portions in the inflated as well as deflated state.

Accordingly, it is an object of the invention to provide an improved dilatation catheter.

It is another object of the invention to provide a balloon catheter in which expansion of the balloon does not result in longitudinal change of balloon position within a blood vessel during a medical procedure.

A further object of the invention is to provide a balloon catheter which does not curl as a result of inflation.

Still another object of the invention is to eliminate the undesirable effects of longitudinal motion of a balloon catheter on the lumen of a blood vessel during inflation.

Still a further object of the invention is to provide a catheter having a balloon portion with improved dimensional stability when inflated.

Yet another object of the invention is to provide a catheter having a balloon portion which will return to its original dimension rapidly upon deflation.

Yet a further object of the invention is to provide a balloon catheter which does not provide surface rotation upon inflation of the balloon portion.

Yet another object of the invention is to provide a balloon catheter which has a smooth outer surface for the balloon portion and the transition portions in the uninflated as well as inflated state.

Still other objects and advantages of the invention will in part be obvious and will in part be apparent from the specification.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE INVENTION

Figure 1:
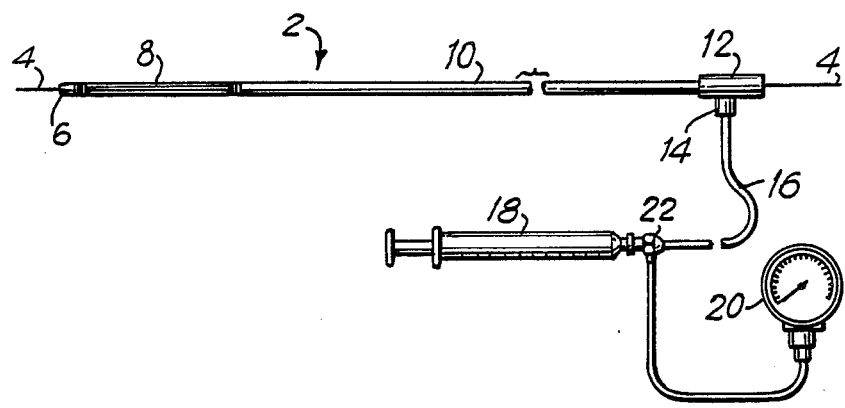
FIG. 1 is a plan view of a balloon catheter fabricated according to the teachings of the invention, showing an attachment for supplying inflating fluid under pressure.

FIG. 1 shows a catheter, generally designated 2 and having a distal tip 6, with a guide wire 4 positioned in an inner passageway 3 of catheter 2. Catheter 2 has a balloon portion 8 formed in a portion of longitudinal shaft 10. As catheter 2 is inserted percutaneously in a patient, tip 6 first passes along guide wire 4, being followed by balloon portion 8 and as much of catheter shaft 10 as is necessary for balloon portion 8 to reach the desired region in the artery.

A proximal catheter fitting 12 remains external of the patient and is attached to a pressure tube 16 into which fluid can be forced by means of a syringe 18 or other inflation device via a connecting tee 14. Pressure in the fluid can be monitored by means of a guage 20 which is connected to pressure tube 16 by means of a second connecting tee 22. A guiding catheter which is also conventionally using a placing the balloon catheter in position in the blood vessel is not illustrated.

Figure 2A:
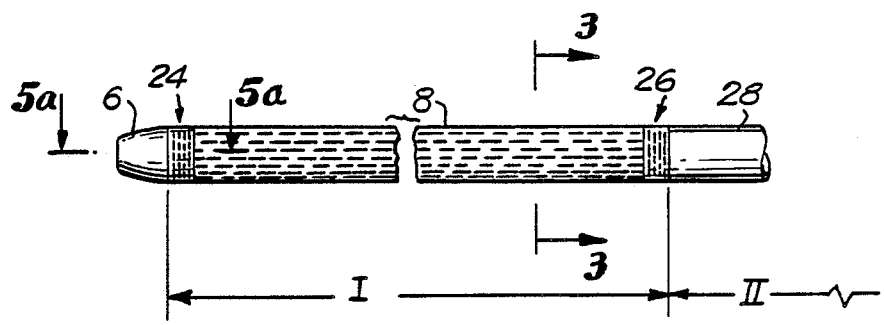
FIG. 2a is a plan view of the balloon and transition portions showing the balloon in an uninflated condition.
Figure 2B:
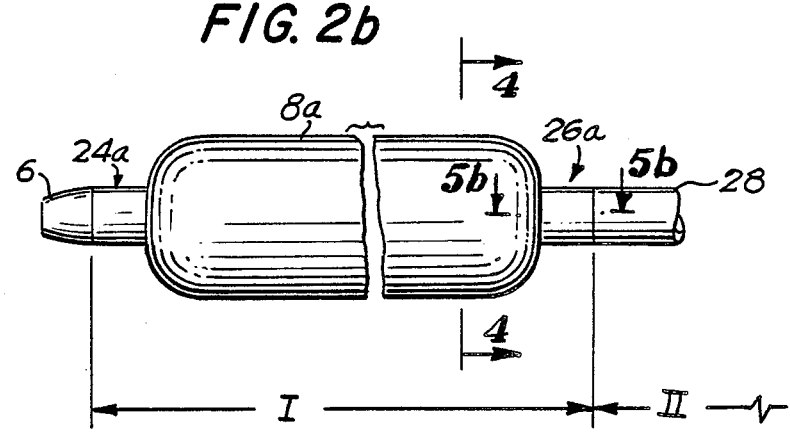
FIG. 2b is a plan view of the catheter of FIG. 2a wherein the transition portions of the catheter are sewn to the balloon portion shown in an inflated condition.
Figure 2C:
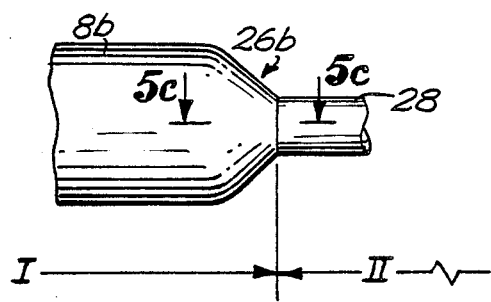
FIG. 2c is a plan view of the catheter of FIG. 2a wherein the transition portions are integrally formed with the balloon portion shown in an inflated condition.
Figure 5A:
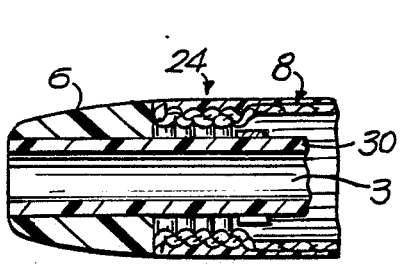
FIG. 5a is a cross-sectional view along lines 5a—5a of FIG. 2a showing detail of the distal balloon connection in an uninflated condition.
Figure 5B:
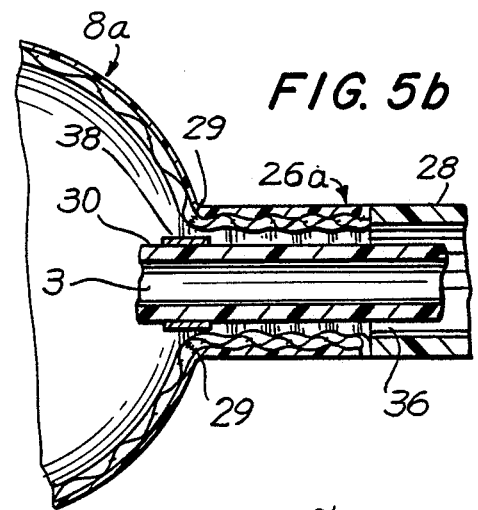
FIG. 5b is a cross-sectional view along lines 5b—5b of FIG. 2b showing detail of the proximal balloon connection.

Reference is now made to FIGS. 2a, 2b and 2c for a general description of the balloon region of catheter 2. FIG. 2a is a plan view showing catheter balloon 8 in an uninflated condition and FIGS. 2b and 2c show balloon 8 in an inflated condition. The distal end of catheter 2 includes a tapered or conical distal tip 6 which may be be made of plastic, a distal connecting portion 24, balloon portion 8, a proximal connecting portion 26 and an outer shaft tube 28. As detailed in FIG. 5a, tip 6 is formed with a tapered, angular ring within which the distal end of inner catheter tube 30 is sealed. Distal connecting portion 24 and proximal connecting portion 26 are of the same pleated construction. In FIG. 2b a distal connecting portion 24a and a proximal connecting portion 26a are sewn to balloon portion 8a at stitching 29 and are capable of yielding longitudinally, as detailed in FIGS. 2b and 5b, while substantially maintaining the same outer diameter. In FIG. 2c, transition portion 26b is shown as formed integrally with balloon portion 8b and expands in a radial direction at the connections with balloon portion 8b.

Figure 7:
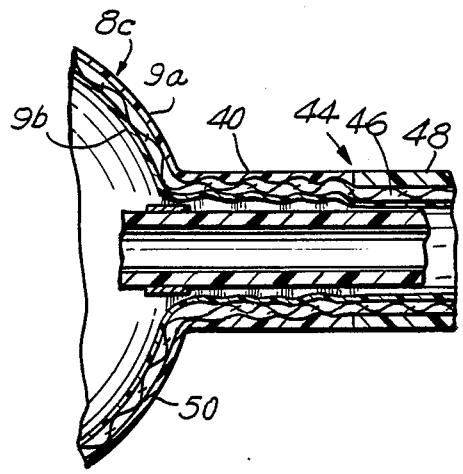
FIG. 7 is a cross-sectional view illustrating a portion of an alternative construction of the catheter in an inflated condition.

In order to provide for diametric expansion from the uninflated condition of FIG. 2a to the inflated condition of FIG. 2b, substrate 7 of balloon portion 8 is pleated in the length-wise direction so as to provide a low value of circumferential stiffness until a specific radius is obtained, and to have an abrupt rise in circumferential stiffness thereafter. Substrate 7 is treated with an elastomeric material 9, such as polyurethane or other biologically acceptable elastomers to coat or impregnate substrate 7. Alternatively, the elastomer may be in the form of inner and outer sleeves 9a and 9b as shown in FIG. 7. In addition, the wall of balloon portion 8 has a high stiffness in the axial direction, so that there is little significant change in length along most of the length of balloon portion 8 when the balloon is inflated. These objective are met by crimping the wall of the substrate of balloon portion 8 to provide longitudinally stiff elements which yield circumferentially until a predetermined diameter is reached.

Figure 3:
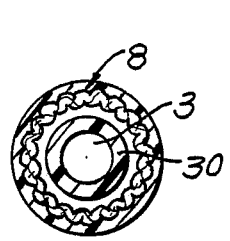
FIG. 3 is a cross-sectional view along lines 3—3 of FIG. 2a showing the central portion of the balloon in an uninflated condition.
Figure 4:
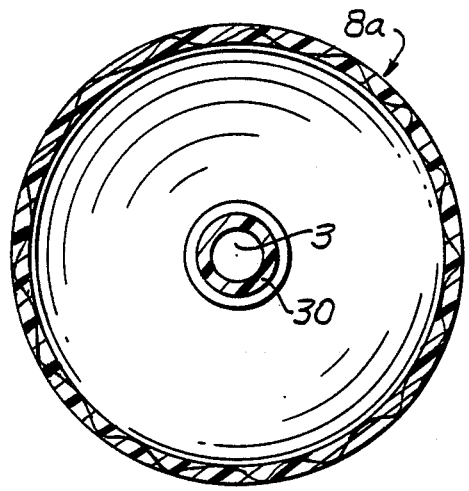
FIG. 4 is a cross-sectional view along lines 4—4 of FIG. 2b, showing the balloon portion in an inflated condition.

As can be seen by comparing the uninflated and the inflated balloons of FIGS. 3 and 4, respectively, the crimped fabric substrate of balloon portion 8 results in its compact stowage around inner catheter tube 30. The uninflated balloon portion 8 has an outer diameter which is the same as that of catheter tip 6 and of shaft tube 28, facilitating movement of catheter 2 within the artery of a patient. When inflated, the flattening out of the accordian-pleat-like crimps in the wall of balloon portion 8 (FIGS. 4 and 5b) limits further expansion thereof. The pleated structures are readily fabricated, for example, by crimping a tube of textile fabric in the circumferential or the longitudinal direction, respectively and coating with elastomer.

Even though the high axial stiffness of balloon portion 8 will prevent substantial changes in the active length during inflation, some change in overall length is unavoidable in the regions of attachment of the balloon portion to the catheter tip and to the distal end of the shaft tube. To avoid the need for a compensating retraction of catheter tip 6, extendable connection portions 24 and 26 are provided at each end of balloon portion 8. These portions extend axially when the balloon is inflated offsetting any retraction of the ends of balloon portion 8 so that tip 6, balloon portion, and outer tubing 28 of catheter 2 remain stationary while the balloon is being inflated.

Figure 5C:
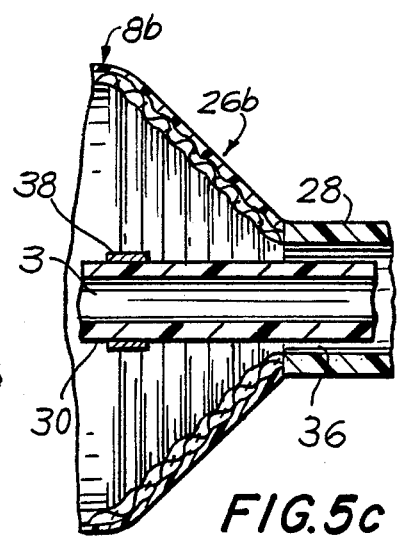
FIG. 5c is a cross-sectional view along lines 5c—5c of FIG. 2c showing detail of the proximal balloon connection.
Figure 6:
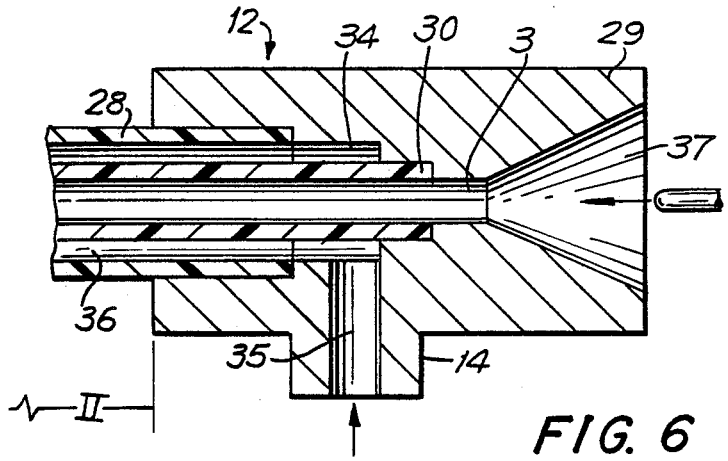
FIG. 6 is a cross-sectional view of the proximal portion of the catheter shaft, showing the catheter fitting.

As depicted in FIGS. 5 and 6, connecting portions 24 and 26 are both constructed in the form of cylinders which, after longitudinal crimping and coating, have an outer diameter which corresponds to that of shaft tube 28. As with the wall of balloon portion 8, the wall of each connecting portion is formed of a coated crimped fabric; but these structures resist radial expansion while yielding longitudinally. The distal ends of connecting portions 24 and 26 are respectively bonded to the proximal wall of catheter tip 6 and are fixed to or integrally formed with the proximal end of balloon portion 8 while the proximal ends of the connecting portions are respectively fixed to or integrally formed with the distal end of balloon portion 8 and bonded to the distal end of outer catheter tubing 28, respectively.

FIG. 6 depicts, in partial cross-section, the proximal fitting 12 which is used with catheter 2. Fitting 12 includes a solid block 29 having an axial opening in which the proximal end of inner catheter tube 30 is seated. A passageway 34 surrounds inner tube 30, and communicates with passageway 36 within outer catheter tube 28. Communicating radially with passageway 34 is a fluid supply passageway 35 by means of which fluid under pressure is fed into catheter 2. A conical aperture 37 communicates axially with inner catheter passageway 3 through which guide wire 4 is threaded.

In use, balloon portion 8 of catheter 2 is inflated by forcing fluid into catheter 2 via tube 16 (FIG. 1). The fluid flows from tube 16 into connecting tee 14 of catheter fitting 12 (FIG. 6) where it passes into an annular space 34 around the proximal end of inner catheter tube 30. From annular space 34, the fluid flows into an annular space 36 between inner tube 30 and outer tube 28, whence it flows past a radio-opaque marker band 38 (FIG. 5b), through proximal connecting portion 26 and into balloon portion 8, and finally into distal connecting portion 24. When balloon portion 8 expands under pressure of the fluid, it does so until further expansion in diameter is limited by the flattening of pleats of fabric substrate 7 into a substantially cylindrical balloon wall. At the same time, elongation of connecting portions 24 and 26 offsets any small longitudinal shortening of balloon portion 8. When the angioplasty procedure has been completed, fluid is withdrawn from catheter 2 by reversing the action of syringe 18 and balloon portion 8 and connecting portions 24 and 26 readily resume their original configurations.

In an alternative form of construction shown in FIG. 7, the distal connecting portion (not shown), a proximal connecting portion 40, and a balloon portion 8c are fabricated as before, being integrally formed, bonded or sewn together. However, the proximal end of proximal connecting portion 40 is joined at 44 to the distal end of a long tube 46 of a Dacron fabric of appropriate inner and outer diameter. Fabric tube 46 is threaded into an equally long outer tubing 48 of Teflon/FEP of appropriate diameter and bonded thereto with the connecting portions and balloon portion 8c extending forward thereof. The outer surfaces of the connecting portions and balloon portions of the catheter prepared in accordance with this embodiment are dip-coated with polyurethane 50 so that the total outer diameters of these components, when the balloon portion is uninflated, matches that of the shaft section 48. After inner catheter tube 30, of appropriate diameter, has been passed into the foregoing assembly, the distal end of the inner tube is bonded, as was tube 30 in the first embodiment, to the distal end of the distal connecting portion (not shown).

Figure 8A:
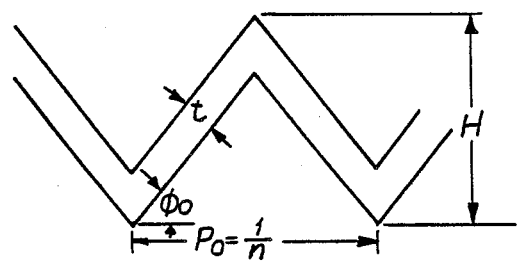
FIGS. 8a-8e are schematic representatives of crimped structures useful in fabricating the balloon portion in accordance with the invention.
Figure 8B:
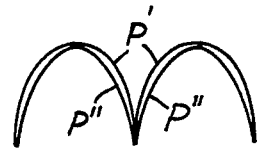
Figure 8C:
Figure 8D:
Figure 8E:
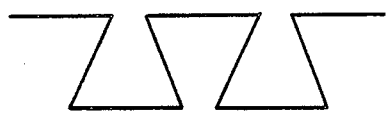

FIG. 8a is a view in cross-section of a "triangular" crimp geometry which may be employed in forming the accordian-like walls of balloon portion 8 and of expansion sections 24, 26 or 40; FIGS. 8a–8e are schematic representations showing various geometric forms of the crimps which may be employed in the structures prepared in accordance with the invention. In FIG. 8b the crimps are formed into parabolas p' and p'' of differing shape. FIG. 8d is the limiting case for the preceding embodiments in which the crimps are of substantially rectangular cross-section. FIG. 8e illustrates a folded structure in which the crimping forms a wall of a series of sequentially inverted frustums of triangles. The foregoing geometries lend themselves readily to mathematical analysis for comparison of relative structural advantage.

It will be seen that, when using the straight-sided, triangular crimp of FIG. 8a, the radial depth H is proportional to the pitch distance $P_0$ when crimp angle $\phi_0$ is kept constant so that the small pitch distances desirably reduce the radial depth H of a crimp section, providing a more compact structure while still providing the same degree of expansion. When the fabric thickness is taken into account in designing such a triangular configuration, the thickness as well as the fabric type, e.g. the type of yarn, weave, etc., must be chosen to meet the following criteria:

$$\sigma_\theta > \frac{\psi (D1 + D2)}{4t} \quad (1)$$

$$\sigma_z > \frac{\psi (D1 + D2)}{8t} \quad (2)$$

where $\sigma_\theta$ and $\sigma_z$ respectively are the circumferential tensile strength and the axial tensile strength of the fabric, $\psi$ is the desired burst pressure, D1 is the inner diameter of the inflated balloon, D2 is the outer diameter of the inflated balloon, and t is the thickness of the fabric used for balloon construction. The right-hand sides of the equations represent the stresses in the wall of the inflated balloon in the circumferential and the axial direction, respectively.

Further, given a minimum wall thickness(t) of the inflated balloon calculated by equation (1) and (2), the unstretched crimp angle $\phi_0$ for a given number of crimps pwer unit length (n) and a given undeformed crimp height (H) can be determined by trial-and-error calculation from the equation:

$$2n \left( H - \frac{t}{\cos \phi_0} \right) = \tan \phi_0 \quad (3)$$

which is derived from the geometry of the structure.

The ratio $\lambda$ of fully extended crimp length to initial (uninflated) crimp length is related to $\phi_0$ by the equation;

$$\lambda = (\cos \phi_0)^{-1} \qquad (4)$$

Illustrative calculations are presented below.

For a number of crimps per mm n=2.25, a height H of 0.9 mm, and a thickness t of 0.2 mm, trial-and-error solution of equation (3) and equation (4) yield $\phi_0 \sim 65°$ and $\lambda = 2.37$. Increasing the value of n to 5.0, while keeping $\phi_0 = 65°$ and t=0.2 mm, yields a height H of 0.687 mm, which is 24% less than that of the first calculated example, thus reducing the profile (outside diameter) of the uninflated balloon.

The uninflated outside diameter OF of the balloon, given a predetermined inside diameter ID and an uninflated crimp height of H is determined as follows:

$$OD = ID + 2H$$

Thus, for an uninflated ID of 0.5 mm and the above calculated H=0.687, the uninflated OD of the balloon is 1.87 mm plus the thickness of the polyurethane coating and the inflated OD is 2.37×(0.5+0.687), or 2.813 mm plus the thickness of the polyurethane coating.

If a fabric thickness of 0.1 mm provides adequate burst strength, then, given H=0.687 mm, n=5, and t=0.1 mm, trial-and-error solution of equation (3) yields values of $\phi_0 = 73.4°$ and $\lambda = 3.5$. For the same uninflated balloon OD, the inflated OD now is 4.155 mm plus the thickness of the polyurethane coating. Although the above calculation is shown for triangular crimps, the other crimp geometries will yield much higher $\lambda$ values:

$$( \text{\jmath\Gamma\Gamma} > \frown\frown > \frown > \cap > \wedge ).$$

By similar calculations, it can be shown that for identical crimp heights and pitches, the parabolic (FIG. 8b) crimp geometry will yield higher expansion in diameter than the triangular crimp geometry, while the "frustum of triangle" crimp geometry (FIG. 8d) will yield a still higher diameter. On the other hand, for the same expandability and the same crimp pitch, the parabolic crimp geometry will require less crimp height than the triangular crimp geometry and the "frustum of triangle" crimp geometry will require still less, providing lower uninflated profiles for the balloon portion of the catheter for a given uninflated balloon inside diameter.

In the alternative, for a given uninflated balloon outside diameter, reduced crimp height results in increased inside diameter of the uninflated balloon, allowing use of a larger diameter inner tube and providing improved fidelity in distal pressure wave monitoring. The frustum of triangle structure of FIG. 8e yields the highest ratio of fully inflated balloon diameter to uninflated balloon diameter for given value of crimp height and crimp pitch. At the same time, the frustum of triangle crimp geometry results in the smallest required crimp height for the desired expandability and the given crimp pitch, yielding the lowest uninflated profile for the balloon for a given uninflated balloon inner diameter. Where the catheter is also to be used for distal pressure wave monitoring, the smaller frustum of triangle crimp geometry for a given uninflated balloon outer diameter also permits increasing the inner diameter of the uninflated balloon, thus allowing use of an inner tube having larger inner and outer diameters, thereby improving the fidelity of pressure wave transmission.

The balloon portion and connecting portions of the balloon catheter constructed in accordance with the invention can be fabricated using suitable biologically compatible materials. The fabric substrate can be knitted or woven polyester which is appropriately crimpled and then coated with an elastomeric material. The elastomer must provide surface smoothness and be non-thrombogenic. The adjoining fabric sections can be sewn together or formed integrally and the free ends of the expansion portions appropriately bonded to the rear surface of the catheter tip and the distal surface of the catheter shaft tube as described above. Other structures can, of course, be employed.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A dilatation catheter, comprising:
   a length of a tubular shaft of flexible material having a longitudinal axis;
   an inner tubular flexible member coaxially disposed in the shaft and having a distal portion projecting therefrom;
   a balloon portion formed at the distal end of the flexible shaft, the balloon portion being capable of expanding radially to a predetermined diameter with minor axial movement when subjected to internal pressure to provide a balloon, the balloon portion fixed to the distal end of the tubular flexible shaft and the distal end of the inner tubular flexible member; and
   a transition portion at each end of the balloon portion for coupling the balloon portion to the distal end of the inner tubular flexible member and the distal portion of the tubular flexible shaft, the transition portion being capable of longitudinal extension in response to a minor longitudinal contraction at the two ends of the balloon portion to reduce the axial movement when the balloon portion is inflated.

2. The dilatation catheter of claim 1, in which the balloon portion is formed from a fabric substrate and a fluid impermeable elastomer.

3. The dilatation catheter of claim 1, in which the transition portion is formed from a fabric substrate and a fluid impermeable elastomer.

4. The dilation catheter of claim 1, in which the balloon portion is formed with radial crimps running length-wise about the circumference of the balloon portion.

5. The dilatation catheter of claim 1, in which the transition portion is formed with longitudinal crimps.

6. The dilatation catheter of claim 1, in which the balloon portion is formed with a plurality of circumferential crimps running length-wise and the transition portions are formed with a plurality of longitudinal crimps across the length of the catheter.

7. The dilatation catheter of claim 6, in which the baloon portion and the transition portions are formed from a fabric substrate and an elastomer.

8. The dilatation catheter of claim 4, in which the transition portion is formed from a fabric coated with an elastomer.

9. The dilatation catheter of claim 5, in which the balloon portion is formed from a fabric coated with an elastomer.

10. The dilatation catheter of claim 6, in which the crimps have a triangular cross-section.

11. The dilatation catheter of claim 6, in which the crimps have a curvilinear cross-section.

12. The dilatation catheter of claim 6, in which the crimps have a cross-section in the form of a frustum of triangle.

13. The dilatation catheter of claim 7, in which the fabric is polyester.

14. The dilatation catheter of claim 7, in which the polyester is coated with polyurethane.

15. The dilatation catheter of claim 1, in which the inner member includes a distal tip, the shaft having a distal transition portion, a proximal transition portion, and a balloon portion therebetween, the distal end of the distal transition portion coupled to the distal tip, the proximal end of the proximal transition portion fixed to the outer flexible shaft, and the balloon portion between the connecting portions.

16. The dilatation catheter of claim 6, further including a radio-opaque member to aid in positioning the catheter during use.

17. The dilatation catheter of claim 16, wherein the fabric substrate is a dacron fabric and the elastomeric material is a polyurethane.

18. The dilatation catheter of claim 2, wherein the fabric substrate is coated with the elastomer.

19. The dilation catheter of claim 2, wherein the fabric substrate is impregnated with the elastomer.

20. The dilatation catheter of claim 2, wherein the elastomer is in the form of an inner sleeve and an outer sleeve disposed about the fabric substrate.

21. The dilatation catheter of claim 3, wherein the fabric substrate is coated with the elastomer.

22. The dilatation catheter of claim 3, wherein the fabric substrate is impregnated with the elastomer.

23. The dilatation catheter of claim 3, wherein the elastomer is in the form of an inner sleeve and an outer sleeve disposed about the fabric substrate.

24. A dilatation catheter, comprising:
a length of a tubular shaft of flexible material having a longitudinal axis;
an inner tubular flexible member coaxially disposed in the shaft and having a distal portion projecting therefrom;
a balloon portion formed at the distal end of the flexible shaft, the balloon portion formed with a plurality of circumferential crimps running length-wise being capable of expanding radially to a predetermined diameter with minor axial movement when subjected to internal pressure to provide a balloon, the balloon portion fixed to the distal end of the tubular flexible shaft and the distal end of the inner tubular flexible member; and
a transition portion end of the balloon portion surrounding the inner flexible member formed with a plurality of longitudinal crimps across the length of the catheter for coupling the balloon portion to the distal end of the inner tubular flexible member and the distal portion of the tubular flexible shaft, the transition portion being capable of longitudinal extension in response to a minor longitudinal contraction at the two ends of the balloon portion to reduce the axial movement when the balloon portion is inflated.

25. The dilatation catheter of claim 24, in which the balloon portion and the transition portions are formed from a fabric substrate and an elastomer.

26. The dilatation catheter of claim 24, in which the crimps have a triangular cross-section.

27. The dilatation catheter of claim 24, in which the crimps have a curviliner cross-section.

28. The dilatation catheter of claim 24, in which the crimps have a cross-section in the form of a frustum of triangle.

29. The dilatation catheter of claim 25, in which the fabric is polyester.

30. The dilatation catheter of claim 25, in which the polyester is coated with polyurethane.

31. The dilatation catheter of claim 24, further including a radio-opaque member to aid in positioning the catheter during use.

32. The dilatation catheter of claim 31, wherein the fabric substrate is a dacron fabric and the elastomeric material is a polyurethane.

33. A balloon catheter for introduction into a blood vessel, comprising:
an inner tube having a longitudinal axis;
an outer tube in coaxial relation to the inner tube;
the inner diameter of the outer tube being larger than the outer diameter of the inner tube so that the two tubes form an annular space between the tubes, and the distal end of the inner tube extending beyond the distal end of the outer tube with the distal end of the outer tube sealed to the inner tube;
the outer tube formed of a flexible material and having a balloon portion and a transition portion at each end of the balloon portion disposed at the distal end of the outer tube; the balloon portion and transition portions formed from a fabric substrate and a fluid impermeable elastomeric material;
the balloon portion formed with a plurality of circumferential crimps running length-wise along the axis;
the transition portion formed with a plurality of longitudinal crimps across the axis;
the balloon portion adapted to be inflated to a predetermined diameter when subject to internal pressure to provide a balloon; and
the transition portions longitudinally extending to compensate exactly for minor longitudinal contraction at the two ends of the balloon portion when the balloon is inflated whereby the baloon portion is not displaced longitudinally in the blood vessel.

* * * * *